United States Patent [19]
Wagner et al.

[11] Patent Number: 5,827,717
[45] Date of Patent: Oct. 27, 1998

[54] MICROORGANISMS THEIR USE AND METHOD OF PRODUCING L-α-AMINO ACIDS

[75] Inventors: Fritz Wagner, Brunswick; Dirk Volkel, Salzgitter; Andreas Bommarius, Frankfurt am Main; Karlheinz Drauz, Freigericht, all of Germany

[73] Assignee: Degussa Aktiengesellschaft, Deutschland, Germany

[21] Appl. No.: 595,214

[22] Filed: Feb. 1, 1996

Related U.S. Application Data

[62] Division of Ser. No. 246,279, May 19, 1994, Pat. No. 5,516,660.

[30] Foreign Application Priority Data

May 19, 1993 [DE]   Germany ............................ 43 16 928.7

[51] Int. Cl.$^6$ ............................... C12N 9/14; C12N 9/90; C12N 5/00; C07H 21/04
[52] U.S. Cl. ...................... 435/195; 435/233; 435/252.3; 435/320.1; 435/325; 435/410; 536/23.2; 935/22
[58] Field of Search .................................. 435/106, 320.1, 435/195, 240.1, 233, 252.3, 325, 410; 536/23.2; 935/22

[56] References Cited

FOREIGN PATENT DOCUMENTS 0 515 698   12/1992   European Pat. Off. ........ C12P 13/04
62-271      1/1987    Japan .

OTHER PUBLICATIONS

Kase, H. et al, (1973) Arg. Biol. Chem 37 (7), 1643–1649.
Harvey W. Blanch, et al., Annals of the New York Academy of Science, vol. 542. Enzyme Engineering 9, pp. 323–329 (1987).
Douglas S. Clark et al., Annals of the New York Academy of Sciences, vol. 672, Enzyme Engineering XI. pp. 478–483 (1992).

*Primary Examiner*—Robert A. Wax
*Assistant Examiner*—Einar Stole
*Attorney, Agent, or Firm*—Cushman Darby & Cushman IP Group of Pillsbury Madison & Sutro LLP

[57] ABSTRACT

The invention relates to novel microorganisms, their use and method of producing L-α-amino acids. In particular, microorganisms DSM 7329 and 7330 are suitable for the production of L-α-amino acids from corresponding hydantoins or carbamoyl-α-amino acids. These novel microorganisms are simple to cultivate and make possible high L-α-amino acid yields from different substrates.

6 Claims, No Drawings

5,827,717

MICROORGANISMS THEIR USE AND METHOD OF PRODUCING L-α-AMINO ACIDS

This is a division of application Ser. No. 08/246,279, filed May 19, 1994, now U.S. Pat. No. 5,516,660.

BACKGROUND OF THE INVENTION

The invention relates to novel microorganisms which are capable, at high specific activities, of converting D- or L- or D,L-5-monosubstituted hydantoins or D- or L- or D,L-N-carbamoyl-α-amino acids into the corresponding, enantiomerically pure L-α-amino acids.

Up to the present, numerous methods have been described in the art concerning the fermentative or enzymatic transformation of N-5-monosubstituted hydantoins into the enantiomerically pure L-α-amino acid (see Syldatk, et al., "Microbial and Enzymatic Production of L-Amino Acids from D,L-5-Monosubstituted Hydantoins," *Biocatalytic Production of Amino Acids and Derivative*, Rozzell, J. D. and Wagner, F., eds., Hanser Verlag, Munich, 1992, pp. 129–176; Yokozeki, et al., (1986), "Optimal Conditions for the Enzymatic Production of L-Aromatic Amino Acids from the Corresponding 5-Substituted Hydantoins," *Agric. Biol. Chem.* 51: 729–736; and Yokozeki, et al., (1986), "Mechanism of Asymmetric Production of L-Aromatic Amino Acids from the Corresponding Hydantoins by Flavobacterium Sp.," *Agric. Biol. Chem.*, 51: 737–746). For instance, this latter reference describes a reaction mechanism for the hydrolysis of 5-arylalkyl hydantoins using the example of 5-benzyl hydantoin with a cleaned-up hydantoinase of Flavobacterium sp. AJ-3912. The relative rates of the forward and of the reverse reactions were determined thereby and it was shown that the forward reaction of D-5-benzyl hydantoin to N-carbamoyl-D-phenyl alanine took place distinctly more slowly than the hydrolysis of L-5-benzyl hydantoin to N-carbamoyl-L-phenyl alanine. No mention was made of the mechanism of the enantioselective hydrolysis of 5-alkyl hydantoins since D,L-5-methyl thioethyl hydantoin was only able to be converted to N-carbamoyl-L-methionine in trace amounts.

SUMMARY OF THE INVENTION

The present invention relates to novel microorganisms which are simple to cultivate and which produce enzymes which are capable of producing L-α-amino acids from D-, L- and/or D,L-5-monosubstituted hydantoin and/or a D-, L- and/or D,L-N-carbamoyl-α-amino acid in relatively large amounts (as compared to the art) and at relatively high rates (as compared to the art). The invention also relates to a corresponding method for producing L-α-amino acids as well as the use of the microorganisms.

The novel microorganisms of the invention are exemplified by DSM 7329 and DSM 7330. These microorganisms constitute novel specimens of the Arthrobacter species.

The invention also relates to a method for producing L-α-amino acids by means of the enzymatic conversion of a D-, L- and/or D,L-5-monosubstituted hydantoin and/or a D-, L- and/or D,L-N-carbamoyl-α-amino acid. The conversion takes place by means of the microorganism(s) DSM 7329 and/or DSM 7330, and/or by means of enzymes produced from these microorganisms.

The present invention also relates to a method of cultivating mutants or variants of microorganism DSM 7329 and/or of microorganism DSM 7330.

The invention further relates to a method of obtaining a gene coding for a carbamoylase, hydantoinase and/or hydantoin racemase.

The invention also relates to a method of inserting a gene coding for a carbamoylase, hydantoinase and/or hydantoin racemase into a microorganism or cell.

DETAILED DESCRIPTION OF THE INVENTION

In the present invention, two novel Arthrobacter microorganisms (DSM 7329 and DSM 7330) were isolated which exhibit a higher productivity than heretofore shown in the art, and which are capable of producing a number of enzymes in amounts such that the cell mass has a very high activity for the methods described above. For instance, these microorganisms can produce L-methionine from D-, and/or L- and/or D,L- of a 5-monosubstituted hydantoin, and/or from the corresponding N-carbamoyl amino acid, and/or from a mixture of the two classes of composition mentioned in connection with the reaction mechanism described below in Scheme 1.

Microorganisms DSM 7329 and DSM 7330 were deposited on Nov. 17, 1992 in the DSM German Collection of Microorganisms and Cell Cultures GmbH, Mascheroder Weg 1 B, D-38124 Braunschweig.

Using the microorganism(s) and/or enzymes obtainable from the microorganism(s), production of L-α-amino acids can occur virtually stereospecifically. With these novel microorganisms, a wide variety of 5-substituted hydantoins can be converted. The corresponding amino acids are obtained according to the reaction scheme described below (Scheme 1). For example, the invention entails a method for producing L-α-amino acids, comprising the step of enzymatically converting one or more of D-5-monosubstituted hydantoin, L-5-monosubstituted hydantoin, D,L-5-monosubstituted hydantoin, a D-, L- and/or D,L-N-carbamoyl-α-amino acid into the corresponding L-α-amino acid, in the presence of one or both of microorganism DSM 7329 and microorganism DSM 7330, or in the presence of enzymes produced from one or both of microorganism DSM 7329 and microorganism DSM 7330.

According to the present invention, the group in the hydantoin can be an alkyl group, branched, cyclic, substituted with one or more heteroatoms, aromatic, heteroaromatic, etc. Problems were presented solely by 5-methyl hydantoin, 5,5-disubstituted hydantoins, multiply substituted phenyl hydantoins such as 5-3'-methyl-4'-amino methylphenyl hydantoin, bulky substituents directly on the hydantoin such as 5-t-butyl hydantoin as well as groups with charged substituents near the hydantoin (such as, for example, 5-β-carboxylethyl hydantoin, 5-γ-amino propyl hydantoin and 5-δ-amino butyl hydantoin).

On the other hand, the invention was able to convert a variety of compounds, including 5-substituted hydantoins with the substituent isopropyl, N-propyl, N-butyl, methyl thioethyl, isobutyl, indolyl methyl, cyclohexyl methyl, benzyl, naphthyl methyl, phenyl. Further, a wide range of substituents are useful in the invention, for example, on the benzyl, p-fluorine, p-chlorine, p-amino, p-methoxy, and p-carboxyl groups. Thus, as persons of ordinary skill in the art would grasp, the 5-substituent in the hydantoin or the N-carbamoyl amino acid does not pose any basic limitations because of the variety of possible substituents and because of the variety of possible functions of the substituents and of the amino acid groups. Basically, all typical 5-substituted hydantoins or corresponding N-carbamoyl amino acids can be useful as substrate in the present invention.

The invention also contemplates mutants or variants obtainable from microorganism DSM 7329 and microorganism DSM 7330, as well as methods of cultivating such mutants or variants. For example, mutants or variants can be effected by selecting spontaneously occurring mutants from cultures of the novel microorganisms. Mutants or variants can also be effected by means of chemical substances and/or radioactive radiation and/or UV light. Mutants or variants can be enriched with elevated and/or more stable enzyme activities from these microorganisms by means of chemical and/or physical mutation or by selection in continuous culturing.

Using microorganism(s) DSM 7329 and/or DSM 7330, and/or the enzymes produced from these microorganisms, L-α-amino acids can be produced by means of enzymatic conversion of a D-, L- and/or D,L-5-monosubstituted hydantoin and/or a D-, L- and/or D,L-N-carbamoyl-α-amino acid. If the method is carried out with either or both of the novel microorganism, it is preferable to use resting or dead microorganisms in order that the microorganisms do not utilize the substrate for themselves. If the method is carried out by means of the enzymes produced from either or both of these microorganisms, this can be achieved using a mash of the microorganisms (obtained, for example, by means of a French press or glass-bead mill), or by using a raw extract or further purified enzymes of the microorganisms.

The invention further entails a method of obtaining a gene coding for a carbamoylase, hydantoinase and/or hydantoin racemase. One or more of these genes may be isolated from one or both of the microorganisms of the invention. As persons of ordinary skill would appreciate, these genes may be useful for, inter alia, the sequence analysis of the genes for the enzymes or for insertion into another microorganism. In the latter instance, the microorganism into which the gene is inserted can be selected for and isolated using conventional methodology, and large amounts of the enzyme(s) produced by the gene can be obtained thereby (using conventional methodology). If desired, the gene can also be inserted into, for instance, an animal or plant cell. The insertion of the gene into an animal cell, plant cell or a microorganisms can be accomplished using methods customary in microbiology, for example, via a vector.

For instance, the invention contemplates microorganism 7329 and microorganism 7330, both of which can contain a gene coding for a carbamoylase, hydantoinase or hydantoin racemase. Using techniques conventional in the art, persons of ordinary skill can insert a gene coding for a carbamoylase, hydantoinase or hydantoin racemase, obtainable from microorganism DSM 7329 or DSM 7330, into a vector. A host cell (such as, for instance, a plant cell or an animal cell) can thereafter be transformed with the vector, using conventional methodology. Thus, a carbamoylase, hydantoinase or hydantoin racemase may be produced by culturing the host cell, under conditions such that the gene is expressed and a carbamoylase, hydantoinase or hydantoin racemase is thereby produced.

Other microorganisms that produce L-α-amino acids are known. However, as described further below, the present invention is novel and distinguishable from anything known or contemplated in the art heretofore.

European patent 0,159,866 B1 describes a bacterium of the genus Arthrobacter sp. DK-200 which can form L-α-amino acids from the corresponding 5-arylalkyl hydantoins and/or from the corresponding N-carbamoyl amino acid. This reference only discloses the synthesis of L-phenylalanine, L-tryptophan and L-tyrosine. There is no teaching of specific enzyme activities or the enzymatic mechanism.

Arthrobacter sp. DK-200 clearly differs from the novel microorganisms Arthrobacter sp. DSM 7329 and DSM 7330 for a number of reasons. For instance, Arthrobacter sp. DK-200 cannot hydrolytically split starch, which is an important physiological feature for identifying types within the Arthrobacter genus. Moreover, the DK-200 strain displays no urease activity and is classified as positive with respect to denitrification. In addition, the DK-200 strain does not grow at temperatures above 33.2° C.

There are significant differences between the physiological features of DK-200 and those of the microorganisms of the invention, such as in the utilization of lactose as carbon source as well as in the formation of acid from sugars (L-arabinose negative and glycerol positive), as can be seen from Table 1.

TABLE 1

Physiological and Bacteriological Features

|  | DSM 7329 | DSM 7330 | DK 200 |
| --- | --- | --- | --- |
| Denitrification | − | − | + |
| Hydrolytic splitting of starch | + | + | − |
| Urease | + | + | − |
| Growth at Temperature | 33° C. | 35° C. | 17.8° C. |
| No Growth at Temperature | >34° C. | >36° C. | >33.3° C. |
| Growth at (% NaCl) | 2% | 5% | 2% |
| No Growth (% NaCl) | >3% | >6% | >5% |
| Formation of acids from sugar: |  |  |  |
| L-arabinose | + | + | − |
| Glycerol | − | − | + |
| Utilization of carbon sources Lactose | + | + | − |

German Patent DE 37 12 539 C2 describes three microorganisms: CW 3 (DSM 3745), CW 4 (DSM 3746) and CW 5 (DSM 3747). These microorganisms are saprophytic, aerobic Coryneform bacteria. These microorganisms are capable of releasing the corresponding aromatic L-α-amino acid from 5-arylalkyl hydantoins and N-carbamoyl-α-amino acids. The German patent also describes the conversion of D-,L-5-methyl thioethyl hydantoin to L-methionine, via D-N-carbamoyl methionine. The patent does not indicate the specific productivity rates of any of the organisms used for these conversions. The conversions of D-N-carbamoyl amino acids to L-amino acids are established by the presence of a racemase on the level of the N-carbamoyl intermediate compounds (See DE 37 12 539, page 2, lines 42–44). Interestingly, a recent publication regarding strain DSM 3747 does not report that any D-N-carbamoyl amino acid participated in obtaining L-amino acids from corresponding D,L-5-monosubstituted hydantoins (cf. Syldatk, et al., "Microbial and Enzymatic Production of L-Amino Acids from D,L-5-Monosubstituted Hydantoin" in: *Biocatalytic Production of Amino Acids and Derivatives* (Rozzell, J. D. and Wagner, F., eds.), Hanser Verlag, Munich, 1992, pp. 129–176).

As is apparent from Table 2, microorganisms DSM 3745, DSM 3746, and DSM 3747 are clearly physiologically distinguishable from the microorganisms DSM 7329 and DSM 7330.

TABLE 2

Physiological and Bacteriological Properties

|  | DSM 7329 | DSM 7330 | DSM 3745 | DSM 3746 | DSM 3747 |
|---|---|---|---|---|---|
| Gram staining | + | + | +/− | − | − |
| Oxidase | − | − | + | − | − |
| No Growth over Temperature | 34° C. | 36° C. | 37° C. | 35° C. | 35° C. |
| Formation of acids from sugar: | | | | | |
| L-arabinose | + | + | + | − | + |
| D-sorbite | + | + | − | − | − |
| Utilization of carbon sources: | | | | | |
| Glycerol | − | − | + | + | + |
| Starch | − | − | + | + | + |
| Citric acid | − | − | + | + | + |

A number of methods are know for producing aliphatic L-α-amino acids starting from 5-alkyl hydantoins or the corresponding N-carbamoyl amino acids. In particular, German patent DE 37 02 384 A1 (corresponding to U.S. Pat. No. 5,071,752) describes the formation of L-amino acids from the corresponding 5-substituted hydantoins using the example of L-leucine, L-valine and L-cysteine with the microorganism Nocardia spec. DSM 3306. However, this patent does not disclose either a specific activity or a mechanism for the hydantoin hydrolysis.

According to Japanese patent Sho 55-29678, a *Corynebacterium sepedonicum* is allowed to act on L- or D,L-N-carbamoyl methionine, which causes the L-N-carbamoyl methionine contained in the substrate mixture to be converted into L-methionine. However, according to this method, only the L-enantiomeric substrate can be converted into L-methionine, whereas the D-N-carbamoyl methionine is not converted.

The reference Guivarch et al., ("Obtention D'Amino Acides Optiquement Actifs A L'aide D'Hydantoinases", *Bull. Soc. Chim. Fr.* No. 1–2, pages 91–95 (1980)), describes the formation of L-methionine from D,L-5-methyl thioethyl hydantoin with *Arthrobacter ureafaciens*, during which a racemization is assumed on the intermediate stage of D- and L-N-carbamoyl methionine. This reaction path differs from the reaction path in the novel microorganisms DSM 7329 and DSM 7330.

Japanese patent (B 2) Hei 4-39316 describes two novel Arthrobacter spec. DP-B-1001 and DP-B-1002 which form the corresponding L-amino acids from 5-substituted hydantoins and from N-carbamoyl amino acids regardless of whether they are present in the D-, L-, D,L form or as a mixture. This patent does not specify the mechanism of the reaction. However, the microorganisms described therein differ considerably in their physiological features from organisms DSM 7329 and DSM 7330, as can be recognized from Table 3. Moreover, there are distinct differences in the specific activities for the conversion of D-N-carbamoyl methionine to L-methionine, as is indicated in Table 4.

TABLE 3

Physiological and Bacteriological Qualities

|  | DSM 7329 | DSM 7330 | 1001 | 1002 |
|---|---|---|---|---|
| Hydrolytic splitting of starch | + | + | − | − |
| Growth at Temperature | 33° C. | 35° C. | 30° C. | 30° C. |
| No Growth at Temperature Over | 34° C. | 36° C. | 37° C. | 37° C. |
| Growth at (% NaCl) | 2% | 5% | 2% | 2% |
| No Growth over (% NaCl) | 3% | 6% | 5% | 5% |
| Nutrient requirement | − | − | biot. | biot. |
| Utilization of malonate | + | + | + | + |
| Formation of acid from sugar: | | | | |
| D-sorbite | + | + | − | − |
| Inosite | + | + | − | − |
| Glycerol | − | − | + | + |
| Utilization of carbon sources: | | | | |
| D-sorbite | + | + | − | − |
| glycerol | − | − | + | + |
| Adonite | − | +/− | − | − |
| Ethanol | + | + | − | − |
| β-alanine | + | − | + | − |
| L-ornithine | + | + | − | − |
| L-threonine | − | + | + | + |
| L-valine | + | − | − | − |
| Acetic acid | − | − | + | + |
| D,L-lactic acid | − | − | + | + |
| Propionic acid | − | − | + | + |
| meso-tartaric acid | − | + | − | − |
| m-hydroxybenzoic acid | − | − | + | + |
| p-hydroxybenzoic acid | − | − | + | + |
| Malonic acid | + | + | + | − |
| Succinic acid | − | − | + | + |
| Citric acid | − | − | + | + |
| Gluconic acid | − | − | + | + |
| Fumaric acid | + | − | + | + |
| Uric acid | − | + | − | − |

The specific activities of entire cells were calculated according to the following equation:

$$A_{spec.} = \frac{\text{mmole or g converted substrate}}{\text{g BFM} \cdot \text{h}}$$

TABLE 4

According to JP (B 2) Hei 4-39316, the Japanese strain DP-B-1001 has the following specific activities for D-N-carbamoyl methionine (D-CM):

$$A_{spec.} = \frac{2.0 \text{ (mmoles)}}{10 \text{ (g BFM)} \cdot 48 \text{ (h)}} = 0.00417 \text{ (mmole/g BFM} \times \text{h)}$$

(BFM = bacterial wet mass)
Under identical conditions strain DSM 7330 has the following specific activities for D-N-carbamoyl methionine:

$$A_{spec.} = \frac{2.6 \text{ (mmoles)}}{10 \text{ (g BFM)} \cdot 21 \text{ (h)}} = 0.0124 \text{ (mmole/g BFM} \times \text{h)},$$

This shows an increase in the specific activities for D-CM under the conditions indicated in the Japanese patent, Example 1, by a factor of 3.3 relative to (g/g BFM × h).
Using another buffer (0.1 M Na-carbonate buffer, pH 8.5) and doubling the substrate, a specific activity was determined as follows $$A_{spec.} = \frac{5.2 \text{ (mmoles)}}{10 \text{ (g BFM)} \cdot 21 \text{ (h)}} = 0.0248 \text{ (mmole/g BFM} \times \text{h)}$$

This shows a futher increase in the specific activity of D-CM of a factor of 6.5.
Under altered conditions (0.2 M tris/HCl buffer, pH 8.0, 30° C., without gassing and without

TABLE 4-continued other additives), the following specific activity of D-CM was determined:

$$A_{spec.} = \frac{4.24 \text{ (mmoles)}}{10 \text{ (g BFM)} \cdot 9.33 \text{ (h)}} = 0.045 \text{ (mmole/g BFM} \times \text{h)},$$

This shows a further increase in the specific activity of a factor of 12.

SCHEME 1

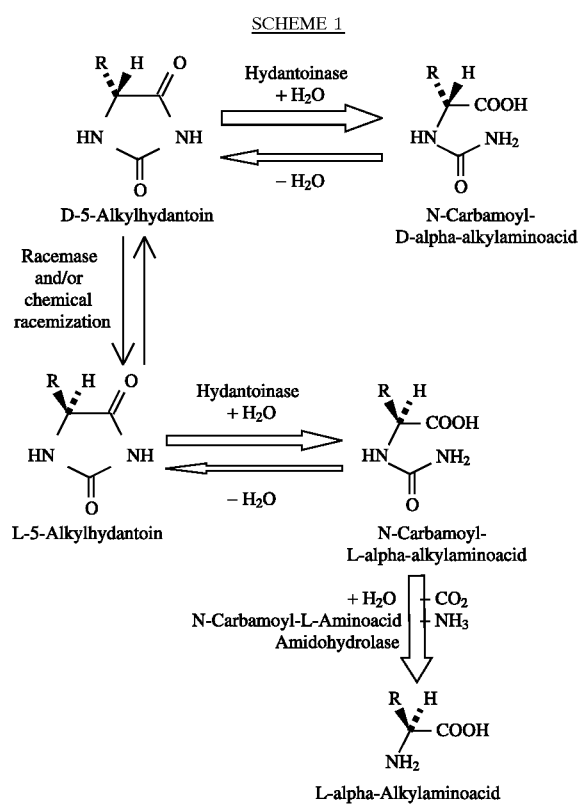

As contemplated by the invention "alkyl" is mentioned only by way of example for the substrate spectrum cited above. The thickness of the arrow indicates the rates found.

The invention is explained in further detail in the following non-limiting examples, which are included for illustrative purposes only.

EXAMPLE 1

Isolation of the Microorganisms 50 ml of a synthetic medium containing D,L-5-methyl thioethyl hydantoin (as the sole source of nitrogen) was made as follows:

| | |
|---|---|
| $KH_2PO_4$ | 1.0 g/l |
| $K_2HPO_4$ | 1.816 g/l |
| $MgSO_4 * 7H_2O$ | 0.123 g/l |
| $CaCl_2 * 2 H_2O$ | 0.017 g/l |
| $FeSO_4 * 7 H_2O$ | 0.006 g/l |
| Glucose | 5.0 g/l |
| D,L-Methylthioethylhydantoin | 1.0 g/l |
| Trace-element solution | 10 ml/l |
| pH: 7.0, | |

The trace-element solution has the following composition:

| | |
|---|---|
| Ethylene diamine tetraacetate (Na+) | 500 mg/l |
| $FeSO_4 * 7 H_2O$ | 200 mg/l |
| $ZnSO_4 * 7 H_2O$ | 10 mg/l |
| $MnCl_2 * 4 H_2O$ | 3 mg/l |
| $H_3BO_3$ | 30 mg/l |
| $CoCl_2 * 4 H_2O$ | 1 mg/l |
| $CuCl_2 * 2 H_2O$ | 1 mg/l |
| $NiCl_2 * 6 H_2O$ | 1 mg/l |
| $Na_2MoO_4 * 2 H_2O$ | 3 mg/l |

1 gram soil samples taken from various locations were incubated in each instance with 50 mls. of the synthetic medium in 500 ml Erlenmeyer flasks with baffles, at 30° C., pH 7.0 and 100 rpms on a rotary mechanical shaker (Braun, Melsungen) for 4 days. Then, 1 ml of each suspension was transferred into fresh, sterile nutrient solution (the synthetic medium) and incubated again for 4 days at 30° C., pH 7.0 and 100 rpms on a rotary mechanical shaker. After 10 cultivation passages each suspension culture was spread out via a dilution series on agar plates on a complex medium (described below) until individual colonies had grown (that is, incubation at 30° C. for three days). The individual colonies were then transferred using conventional procedures into pure cultures.

Composition of the complex medium for the individual microorganism strains:

| | |
|---|---|
| Glucose | 10.0 g/l |
| Commerc. yeast extract | 0.5 g/l |
| Citric acid | 0.5 g/l |
| $MgSO_4 * 7 H_2O$ | 0.1 g/l |
| $CaCl_2 * 2 H_2O$ | 0.05 g/l |
| $KH_2PO_4$ | 1.0 g/l |
| $K_2HPO_4$ | 1.816 g/l |
| Trace-element solution | 10.0 ml/l |
| Agar | 20.0 g/l |
| pH: 7.0 | |

In order to check the enzymatic activity (to determine whether L-α-amino acids were obtained from D,L-5-monosubstituted hydantoins), the pure cultures obtained in this manner were grown as follows in submerged cultures.

100 ml sterile nutrient medium I (described below) were inoculated with a rinse of newly obtained pure culture in a 500 ml Erlenmeyer flask with baffles, and incubated at 30° C., pH 7.0 and 100 rpms on a rotary mechanical shaker for 24 hours. 500 ml sterile nutrient medium II (described below) from the suspension culture obtained in this manner were inoculated in a 2000 ml Erlenmeyer flask with baffles with 10 ml of the seed culture. The inoculated suspension was then cultivated for 35 hours at 30° C., pH 7.2 and at 100 rpms on a rotary mechanical shaker. Thereafter, the cells were centrifuged off and washed twice with 0.9% NaCl solution. The wet cell mass obtained in this manner can either be checked immediately for the enzymatic activity or put in intermediate storage at −18° C. for up to several weeks.

Nutrient medium I has the following composition:

| | |
|---|---|
| Glucose | 10.0 g/l |
| $(NH_4)_2SO_4$ | 6.50 g/l |
| Citric acid | 0.32 g/l |
| $MgSO_4 * 7 H_2O$ | 0.20 g/l |
| $CaCl_2 * 2 H_2O$ | 0.02 g/l |
| $MnCl_2 * 4 H_2O$ | 0.02 g/l |
| $FeSO_4 * 7 H_2O$ | 0.02 g/l |
| $KH_2PO_4$ | 4.54 g/l |
| $K_2HPO_4$ | 7.61 g/l |

Nutrient medium II has the following composition:

| | |
|---|---|
| Glucose | 15.0 g/l |
| Commerc. yeast extract | 1.0 g/l |
| $(NH_4)_2SO_4$ | 6.50 g/l |
| Citric acid | 0.62 g/l |
| $MgSO_4 * 7 H_2O$ | 0.40 g/l |
| $CaCl_2 * 2 H_2O$ | 0.04 g/l |
| $MnCl_2 * 4 H_2O$ | 0.04 g/l |
| $FeSO_4 * 7 H_2O$ | 0.04 g/l |
| $KH_2PO_4$ | 3.40 g/l |
| $Na_2HPO_2 * 2 H_2O$ | 4.42 g/l |
| D,L-5-Indolylmethyl-N-3-methylhydantoin | 0.25 g/l |

The enzymatic activity of the wet cell mass (BFM) obtained in this manner was comparatively tested under the following reaction conditions. 50 mg D,L-5-methyl thioethyl hydantoin and 2.5 grams BFM were added into 50 ml 0.2 molar tris/HCl puffer pH 8.0, and incubated for 24 hours at 30° C. Thereafter, the cell suspension was centrifuged and the clear supernatant examined using HPLC analytic chemistry. Two strains filed in the German Collection for Microorganisms (DSM) under numbers DSM 7329 and DSM 7330 proved to be especially active. They have the following physiological and bacteriological properties, which are specified in Table 5.

TABLE 5

Physiological and Bacteriological Properties

| | DSM 7329 | DSM 7330 |
|---|---|---|
| Properties | | |
| Cell size (L●φ) | (0.3–0.6)* | (0.1–0.2) μm |
| Cell form | short rods | |
| Pleomorphy | + | + |
| Mobility | − | − |
| Flagellation | − | − |
| Gram staining | + | + |
| Spores | − | − |
| Acid resistance | − | − |
| Reduction of nitrates | − | − |
| Denitrification | − | − |
| MR test | − | − |
| VP test | − | − |
| Hydrolytic splitting of starch | + | + |
| Utilization of inorganic nitrogen sources | + | + |
| Formation of stains | − | − |
| Urease | + | + |
| Oxidase | − | − |
| Catalase | + | + |
| Growth at (°C.) | 33 | 35 |
| No Growth over (°C.) | 34 | 36 |
| Growth at (% NaCl) | 2% | 5% |
| No Growth over (% NaCl) | 3% | 6% |

TABLE 5-continued

Physiological and Bacteriological Properties

| | DSM 7329 | DSM 7330 |
|---|---|---|
| Behavior vis-à-vis oxygen (aerobic +) | + | + |
| Nutrient requirement | − | − |
| Gluconic acid oxidation | − | − |
| Utilization of malonate | + | + |
| Formation of acid from sugar: | | |
| L-arabinose | + | + |
| D-xylose | + | + |
| D-glucose | + | + |
| D-mannose | + | + |
| D-fructose | + | + |
| D-galactose | + | + |
| Maltose | + | + |
| Cane sugar (sucrose) | + | + |
| Lactose | + | + |
| Trehalose | + | + |
| D-sorbite | + | + |
| D-mannite | + | + |
| Inosite | + | + |
| Glycerol | − | − |
| Starch | − | − |
| Raffinose | + | + |
| Adonite | − | − |
| Rhamnose | + | + |
| Utilization of carbon sources: | | |
| L-arabinose | + | + |
| D-xylose | + | + |
| D-glucose | + | + |
| D-mannose | + | + |
| D-fructose | + | + |
| D-galactose | + | + |
| Malt sugar (maltose) | + | + |
| Cane sugar (sucrose) | + | + |
| Lactose | + | + |
| Trehalose | + | + |
| D-sorbite | + | + |
| D-mannite | + | + |
| Inosite | + | + |
| Glycerol | − | − |
| Starch | − | − |
| Raffinose | + | + |
| Adonite | − | +/− |
| Rhamnose | + | + |
| Ethanol | + | + |
| β-alanine | + | − |
| D,L-arginine | + | + |
| L-histidine | + | + |
| L-ornithine | + | + |
| L-threonine | − | + |
| L-valine | + | − |
| Formic acid | − | − |
| Acetic acid | − | − |
| Butyrate | − | − |
| D,L-lactic acid | − | − |
| Propionic acid | − | − |
| meso-tartaric acid | − | − |
| D-(−)-tartaric acid | − | − |
| m-hydroxy benzoic acid | − | − |
| p-hydroxy benzoic acid | − | − |
| Glycolic acid | − | − |
| Malonic acid | + | + |
| Succinic acid | − | − |
| Citric acid | − | − |
| α-ketoglutarate | + | + |
| Pyruvate | + | + |
| Glyoxylate | − | − |
| Gluconic acid | − | − |
| Fumaric acid | + | + |
| Pimelic acid | − | − |
| Uric acid | − | + |
| Hippuric acid | + | + |
| Adipic acid | − | − |

TABLE 5-continued

Physiological and Bacteriological Properties

|  | DSM 7329 | DSM 7330 |
|---|---|---|
| Glutaric acid | − | − |
| Panthothenic acid | − | − |
| Laevulinic acid | − | − |
| Citraconic acid | − | − |
| Azelaic acid | − | − |
| Itaconic acid | − | − |
| Betaine | + | + |
| L-methionine | − | − |
| L-tryptophan | − | − |
| L-Phenylalanine | − | − |

Table 6 lists examples of conversions of D,L-5-monosubstituted hydantoins which can be hydrolyzed to L-α-amino acids with the microorganisms of the invention via N-carbamoyl-α-amino acids, in accordance with the reaction mechanism described above in Scheme 1. The same results are found with both strains.

TABLE 6

| R = | Use (mmole) | D,L-Hydantoin (mmole) | N-carbamoyl-derivative (mmole) | L-α-amino acid (mmole) |
|---|---|---|---|---|
|  | 11.5 | — | — | 11.4 |
|  | 12.8 | 0.64 | 3.84 | 8.3 |
|  | 8.7 | — | — | 8.6 |
|  | 10.2 | 1.02 | 3.06 | 6.12 |
|  | 10.5 | — | — | 10.4 |
|  | 8.9 | — | — | 8.8 |

"—" can not be demonstrated

Reaction conditions: The indicated substrate concentration is incubated in 50 ml 0.1M sodium carbonate buffer pH.8.5 with 1.5 grams BFM at 30° C. for 24 hours.

EXAMPLE 2

Cultivation of the Biomass

A 500 ml Erlenmeyer flask with 100 ml sterile nutrient medium I was inoculated with a platinum loop of strain DSM 7330 from a slant agar culture and cultivated on a rotary mechanical shaker at 100 rpms and 30° C. After an incubation time of 24 hours this suspension culture served as inoculum for the second seed culture. Ten 2000 ml Erlenmeyer flasks with 500 ml sterile nutrient medium I were each inoculated with 10 ml of the first seed culture and incubated again 24 hour at 100 rpms and at 30° C. After the incubation time, this seed culture II served as inoculum for a 50 liter bioreactor. The bioreactor was equipped with an intensor system and was charged with 45 liter nutrient medium in accordance with the composition of nutrient medium II and sterilized 30 minutes at pH 6.5 and at temperature of 121° C. and at approximately 1 bar excess pressure. After cooling off to 30° C., the mixture was adjusted with 10% NaOH to pH 7.0 and subsequently inoculated with the suspension culture from seed culture II. The mixture was then cultivated at 30° C. and an agitator speed of 400 rpms and an aeration rate of 0.8 V/V/m. After 18 hours, the wet cell mass was centrifuged off and subsequently washed twice with 0.9% solution of common salt. The wet cell mass obtained in this manner can be used immediately or, after intermediate storage at −18° C., at a later time for enzymatic conversion. 1,725 kg wet cell mass were obtained.

Strain DSM 7329 was grown under the same condition, yielding 1.69 kg wet cell mass, corresponding to 0.34 kg dry cell mass.

EXAMPLE 3

83 grams wet cell mass of DSM 7330 and 20 grams (115 mM) D,L-methyl thioethyl hydantoin were suspended in 1000 ml 0.1M Soerensen buffer pH 8.0 and incubated at 35° C. with $N_2$ gassing in a 2 liter stirred-tank reactor under agitation for 28 hours. The cells were then centrifuged off and the supernatant analyzed with high-pressure liquid chromatography (HPLC). 16.4 grams (110 mM) L-methionine were demonstrated in the supernatant. Yield=95.6% of theory.

EXAMPLE 4

100 grams wet cell mass of DSM 7330 and 10 grams (52 mmoles) D-carbamoyl methionine were suspended in 1000 ml 0.2M tris/HCl buffer, pH 8.0 at 30° C. and incubated without gassing in a 2 liter stirred-tank reactor under agitation for 9 hours. After centrifugation, 6.6 grams (44 mmoles) L-methionine were demonstrated in the supernatant. Yield= 84.6% of theory.

EXAMPLE 5

100 grams wet cell mass of DSM 7329 and 10 grams (52 mmoles) L-carbamoyl methionine were suspended in 1000 ml 0.2M tris/HCl buffer, pH 8.0, 30° C. and incubated without gassing in a 2 liter stirred-tank reactor under agitation for 3.5 hours. After centrifugation, 7.68 grams (51.5 mmoles) L-methionine were demonstrated in the supernatant. Yield=99% of theory.

EXAMPLE 6

100 grams wet cell mass of DSM 7330 and 10 grams (52 mmoles) D,L-carbamoyl methionine were suspended in 1000 ml 0.2M tris/HCl buffer, pH 8.0, 30° C. and incubated without gassing in a 2 liter stirred-tank reactor under agitation for 9 hours. After centrifugation, 7.16 grams (48 mmoles) L-methionine were demonstrated in the supernatant. Yield=92% of theory.

EXAMPLE 7

100 grams wet cell mass of DSM 7330 and 10 grams commercial hydantoin consisting of 10.4 mmoles D,L-carbamoyl methionine and 41.6 mmoles D,L-methyl thioethyl hydantoin were suspended in 1000 ml 0.2M tris/HCl buffer, pH 8.0, 30° C. and incubated without gassing in a 2 liter stirred-tank reactor under agitation for 15 hours. After centrifugation, 7.01 grams (47 mmoles) L-methionine were demonstrated in the supernatant. Yield=90.3% of theory.

EXAMPLE 8

Production of a Raw Extract and Purified Enzyme Solution

Microorganisms DSM 7329 and 7330 were macerated approximately 15 minutes in a glass-bead mill and the biomass subsequently separated by centrifuging. The supernatant was the raw enzyme extract and contained approximately 21 g/l protein.

In order to isolate the hydantoinase contained in the raw extract, it was worked up in accordance with customary methods. This was done in the present instance by means of increasing fractionated precipitation beginning with 1.7M ammonium sulfate, subsequent protamine sulfate (3 g/l) separation and subsequent precipitation of the protein with 2.5M ammonium sulfate. The precleaned product obtained in this manner was cleaned further with column chromatography, during which butyl sepharose, phenyl sepharose and, twice, anion-exchange chromatography (pH 7.8, pH 6.6) were performed in succession. Strain DSM 7329 had a protein content of 0.12 g/l after the first anion-exchange chromatography and strain DSM 7330 a protein content of 0.1 g/l after the second anion-exchange chromatography (according to Bradford). The protein purity was determined by gel electrophoresis.

The raw enzyme extract (21 g/l) and the purified enzyme solution (0.1,g/l hydantoinase) were used in the following examples.

EXAMPLE 9

0.00575 mmole D-methyl thioethyl hydantoin was incubated with 100 µliters enzyme in 900 µliters 0.1M tris/HCl buffer pH 8.5 at 42° C. for 1 hour. After termination of the activity test, 0.00351 mmole D-carbamoyl methionine was measured in the supernatant, which corresponds to a conversion of 61 mole %.

EXAMPLE 10

0.00575 mmole L-methyl thioethyl hydantoin was incubated with 100 µliter enzyme in 900 µliter 0.1M tris/HCl buffer pH 8.5 at 42° C. for 1 hour. After termination of the activity test, 0.000863 mmole L-carbamoyl methionine was measured in the supernatant, which corresponds to a conversion of 15 mole %.

EXAMPLE 11

0.00521 mmole D-carbamoyl methionine was incubated with 100 liter enzyme in 900 liter 0.1M tris/HCl buffer pH 8.5 at 42° C. for 1 hour. After termination of the activity test, 0.000162 mmole D-methyl thioethyl hydantoin was measured in the supernatant, which corresponds to a conversion of 3.1 mole %.

EXAMPLE 12

0.00521 mmole L-carbamoyl methionine was incubated with 100 liter enzyme in 900 liter 0.1M tris/HCl buffer pH 8.5 at 42° C. for 1 hour. After termination of the activity test, 0.000521 mmole L-methyl thioethyl hydantoin was measured in the supernatant, which corresponds to a conversion of 1.0 mole %.

EXAMPLE 13

0.00521 mmole L-carbamoyl methionine was incubated with 100 liter raw extract in 900 liter 0.1M tris/HCl buffer pH 8.5 at 42° C. for 0.5 hour. After termination of the activity test, 0.00521 mmole L-methionine was measured in the supernatant.

All publications mentioned hereinabove are hereby incorporated by reference.

While the foregoing invention has been described in some detail for purposes of clarity and understanding, it will be clear to one skilled in this art from a reading of this disclosure that various changes in form and detail can be made without departing from the true scope of the invention.

We claim:

1. A gene coding for a carbamoylase, hydantoinase or hydantoin racemase, obtainable from microorganism DSM 7329 or DSM 7330.

2. A vector containing the gene of claim 1.

3. A host cell transformed with the vector of claim 2.

4. The host cell of claim 3, wherein the cell is a plant cell.

5. The host cell of claim 3, wherein the cell is an animal cell.

6. A method of producing a carbamoylase, hydantoinase or hydantoin racemase which comprises culturing the cell of claim 3, under conditions such that the gene is expressed and a carbamoylase, hydantoinase or hydantoin racemase is thereby produced.

* * * * *